(12) United States Patent
Williams et al.

(10) Patent No.: US 6,528,072 B1
(45) Date of Patent: Mar. 4, 2003

(54) TOPICAL COMPOSITION FOR SKIN INCLUDING WITCH HAZEL

(76) Inventors: Barbara V. Williams, 9014 E. Stoney Vista Dr., Chandler, AZ (US) 85248-7476; Spencer A. Hassell, 5341 Dunmore Dr., Centerville, OH (US) 45459

( * ) Notice: Subject to any disclaimer, the term of this patent is extended or adjusted under 35 U.S.C. 154(b) by 0 days.

(21) Appl. No.: 09/839,739

(22) Filed: Apr. 20, 2001

(51) Int. Cl.[7] .......................... A61K 6/00; A01N 65/00
(52) U.S. Cl. ....................... 424/401; 424/725
(58) Field of Search .......................... 424/78.02, 78.03, 424/78.06, 78.07, 404, 401, 195.1, 725, 692

(56) References Cited

U.S. PATENT DOCUMENTS

| | | | |
|---|---|---|---|
| 4,590,212 A | * | 5/1986 | Bernstein .................... 514/629 |
| 5,645,854 A | | 7/1997 | Masiz |
| 5,853,751 A | | 12/1998 | Masiz |
| 5,977,325 A | * | 11/1999 | McCarthy et al. ........... 536/4.1 |

OTHER PUBLICATIONS

Balch et al. Prescription for Nutritional Healing; Second Edition, 1997, pp. 78.*

The Merck Index, 1989, 11th Ed. p. 820.*

* cited by examiner

*Primary Examiner*—Leon B. Lankford, Jr.
*Assistant Examiner*—Patricia A Patten
(74) *Attorney, Agent, or Firm*—Parsons & Goltry; Robert A. Parsons; Michael W. Goltry

(57) ABSTRACT

A topical composition applicable to skin for clearing the complexion, including magnesium hydroxide, witch hazel, an analgesic, and alcohol.

12 Claims, No Drawings

TOPICAL COMPOSITION FOR SKIN INCLUDING WITCH HAZEL

FIELD OF THE INVENTION

This invention relates to skin care compositions.

More particularly, the present invention relates to topical compositions for the skin.

In a further and more specific aspect, the instant invention concerns topical compositions for clearing the complexion of acne and blemishes.

BACKGROUND OF THE INVENTION

The skin is considered the largest organ of the human body. It functions as a barrier to separate the human organism from environmental contaminates and detrimental organisms. Skin is an efficient barrier, often necessitating penetration to introduce a substance, such as a pharmaceutical, to underlying tissue. Substances have been developed to penetrate the skin on a molecular level. These substances are employed to carrying other substances through the barrier that is the skin. These substances and compositions are typically not employed to treat the skin, but rather to introduce a substance to the human organism through the skin without mechanical penetration.

Skin also provides an esthetic appeal beyond the merely functional when clear and healthy. Skin care products have long been known and used to promote healthy skin. Care of the skin is typical accomplished through topical application of a composition, as differentiated from a transdermal transport substance. Topical compositions to promote healthy skin include moisturizing lotions, exfoliating compounds, acne lotions, and steroid applications such as hydrocortisone creams. Moisturizing lotions can result in greasy or oily skin. Often, this will result in acne and other blemishes. Additionally, make-up applied over moisturizing lotion or oily skin will often slip into disarray and need to be repaired frequently. Acne lotions often dry the skin, and while somewhat effective, take a long time to act. Cortisone or other steroid creams are extremely effective, but can have adverse long-term effects and are best employed sparingly.

It would be highly advantageous, therefore, to remedy the foregoing and other deficiencies inherent in the prior art.

Accordingly, it is an object of the present invention to provide a new and improved topical composition for skin.

Another object of the invention is to provide a topical composition for clearing the complexion of skin.

And another object of the invention is to provide a topical composition that will prepare the skin for long lasting make-up.

SUMMARY OF THE INVENTION

Briefly, to achieve the desired objects of the instant invention in accordance with a preferred embodiment thereof, provided is a topical composition applicable to skin for clearing the complexion. The topical composition includes magnesium hydroxide, witch hazel, and an analgesic. In a specific aspect, the analgesic includes acetaminophen. The topical composition is proportioned so the magnesium hydroxide includes 10 parts, the witch hazel includes 4 parts, and the analgesic includes less than 0.5 parts.

In a further embodiment, the topical composition includes magnesium hydroxide, witch hazel, an alcohol and an analgesic. In a specific aspect, the alcohol includes isopropyl alcohol. The topical composition is proportioned so the magnesium hydroxide includes 10 parts, the witch hazel includes 1 part, the alcohol includes 1 part and the analgesic includes less than 0.5 parts.

Also provided is a method of preparing the topical composition.

DETAILED DESCRIPTION OF THE PREFERRED EMBODIMENT

This invention includes a topical composition for application to skin. While primarily for use on facial skin, it will be understood that the topical composition can be applied to the skin in substantially any location on the body. The composition quickly reduces the inflammation caused by acne or other blemishes, and promotes healing of the skin. The composition also prepares oily skin for the application of make-up, increasing the effective lifetime of the applied make-up and reducing the necessity of repairing damaged or disarrayed make-up.

The topical composition includes milk of magnesia (magnesium hydroxide), an analgesic such as acetaminophen, an alcohol such as isopropyl alcohol and witch hazel (Hamamelis water). Witch hazel is a liniment made from the twigs and bark of plants from the genus Hamamelis. A mixture of these ingredients forms a composition which when applied to the skin will promote clearing of acne and other blemishes. Inflammation is quickly eliminated with complete healing following soon after. The composition includes generally 10 parts milk of magnesia, 1 part witch hazel, 1 part alcohol, and less than 0.5 part acetaminophen. As will be described presently, alcohol can be omitted. In this instance, the proportion of witch hazel is increased to approximately 4 parts. The amount of each element can vary to some degree, although the effectiveness will be adversely impacted. The most effective mixtures are provided in the following examples.

EXAMPLE 1

Five (5) tablespoons of milk of magnesia (magnesium hydroxide)

2000 mg of acetaminophen 1.5 teaspoons of witch hazel (hamamelis water)

1.5 teaspoons isopropyl alcohol.

This composition is for topical application to skin generally anywhere on the body. However, because it includes alcohol, application on the skin around the eyes may be undesirable. Thus, another embodiment of the present invention omits the alcohol.

Oily skin often requires an individual to re-apply make-up as the make-up essential slides or becomes disarrayed on the skin. Make-up is often employed around the eyes, thus, while the composition of example 1 can be employed, the composition of example 2 is preferred as it does not include alcohol.

EXAMPLE 2

Five (5) tablespoons of milk of magnesia (magnesium hydroxide)

2000 mg of acetaminophen

Two (2) tablespoons of witch hazel (hamamelis water)

While the examples include specific measurements, it will be understood that these measurements indicate the proportions of ingredients and can be enlarged or reduced as desired while maintaining the relative proportions of the ingredients.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A topical composition for clearing skin complexion, comprising:
   10 parts of magnesium hydroxide;
   4 parts of witch hazel; and
   less than 0.5 parts of an analgesic.

2. The topical composition as claimed in claim 1 wherein the analgesic includes acetaminophen.

3. The topical composition as claimed in claim 1 further including an alcohol.

4. The topical composition as claimed in claim 3 wherein the alcohol includes isopropyl alcohol.

5. A topical composition for clearing skin complexion, comprising:
   10 parts of magnesium hydroxide;
   1 part of alcohol;
   1 part of witch hazel; and
   less than 0.5 parts of acetaminophen.

6. The topical composition as claimed in claim 5 wherein the alcohol includes isopropyl alcohol.

7. A method of preparing a topical composition for application to skin to clear a complexion of the skin, comprising the steps of:
   providing 10 parts of magnesium hydroxide;
   providing witch hazel;
   providing less than 0.5 parts of an analgesic; and
   mixing the magnesium hydroxide, the witch hazel and analgesic.

8. The method as claimed in claim 7 wherein the step of providing an analgesic includes providing acetaminophen.

9. The method as claimed in claim 7 further including a step of providing alcohol and mixing alcohol into the composition.

10. The method as claimed in claim 9 wherein the step of providing alcohol includes providing isopropyl alcohol.

11. The method as claimed in claim 9 wherein the step of mixing includes mixing five tablespoons of magnesium hydroxide, 2000 mg of the analgesic, and 2 tablespoons of witch hazel.

12. The method as claimed in claim 7 wherein the step of mixing includes mixing five tablespoons of magnesium hydroxide, 2000 mg of the analgesic, 1.5 teaspoons of witch hazel, and 1.5 teaspoons isopropyl alcohol.

\* \* \* \* \*